United States Patent
Kobayashi et al.

(10) Patent No.: US 6,187,842 B1
(45) Date of Patent: Feb. 13, 2001

(54) SUGAR COMPOUNDS, GELLING AGENTS, GELLING AGENT COMPOSITIONS PROCESSES FOR THE PREPARATION OF THEM, AND GEL COMPOSITIONS

(75) Inventors: Toshiaki Kobayashi, Nara; Kenshi Ando, Uji; Harutomo Nomoto, Kyoto, all of (JP)

(73) Assignee: New Japan Chemical Co., Ltd. (JP)

( * ) Notice: Under 35 U.S.C. 154(b), the term of this patent shall be extended for 0 days.

(21) Appl. No.: 09/297,676

(22) PCT Filed: Nov. 21, 1997

(86) PCT No.: PCT/JP97/04280
  § 371 Date: May 6, 1999
  § 102(e) Date: May 6, 1999

(87) PCT Pub. No.: WO98/23604
  PCT Pub. Date: Jun. 4, 1998

(30) Foreign Application Priority Data

Nov. 28, 1996 (JP) .................................................. 8-334559
Oct. 1, 1997 (JP) .................................................. 9-286169

(51) Int. Cl.[7] .............................. C08K 5/07; C13F 3/00; B01F 17/00
(52) U.S. Cl. .......................... 524/58; 127/30; 127/46.1; 127/53; 127/61; 536/120; 536/124; 516/77; 516/99; 516/902; 424/484
(58) Field of Search .............................. 127/30, 46.1, 53, 127/61; 536/120, 124; 516/77, 99, 902; 524/58; 424/484

(56) References Cited

U.S. PATENT DOCUMENTS 5,964,691 * 10/1999 Mehl ...................... 516/20

FOREIGN PATENT DOCUMENTS 60-16909   1/1985 (JP) .
2-42082    2/1990 (JP) .
3-281684  12/1991 (JP) .
4-337737  11/1992 (JP) .

* cited by examiner

*Primary Examiner*—Nathan M. Nutter
(74) *Attorney, Agent, or Firm*—Larson & Taylor, PLC

(57) ABSTRACT

The invention provides a gelling agent comprising at least one sugar compound selected from the group consisting of sugar compounds represented by the formula (1) and sugar compounds represented by the formula (2).

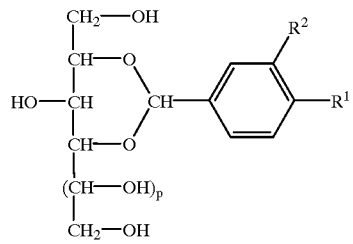

(1)

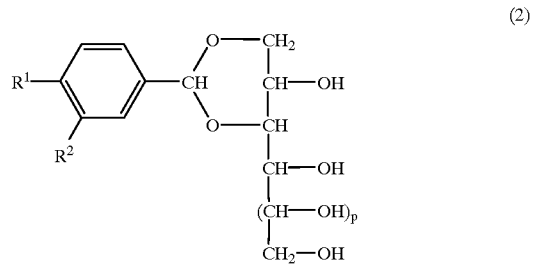

(2)

wherein $R^1$ and $R^2$ are the same or different and each represents an alkyl group having 1 to 3 carbon atoms, an alkoxyl group having 1 to 3 carbon atoms or a halogen atom, and p is 0 or 1.

The gelling agent of the invention is very useful as a gelling agent for an aqueous medium.

23 Claims, No Drawings

SUGAR COMPOUNDS, GELLING AGENTS, GELLING AGENT COMPOSITIONS PROCESSES FOR THE PREPARATION OF THEM, AND GEL COMPOSITIONS

This application claims benefit of priority under 35 USC 371 of PCT/JP97/04280, filed Nov. 21, 1997.

FIELD OF THE INVENTION

The present invention relates to a novel useful sugar compound, a process for preparing the sugar compound, an organic gelling agent containing the sugar compound, a heat-reversible gel prepared using the organic gelling agent, a process for preparing the gel and its use.

The present invention also concerns with a novel useful gelling agent composition which can be used for an aqueous medium, a process for preparing the gelling agent composition, and a gel composition prepared using the gelling agent composition.

The term "gel" used herein refers, from the viewpoint of industrial meaning, to a state of a substance wherein the substance is non-flowable and has a yield value of at least 60 g/cm$^2$ although it contains a large amount of a medium, or to a substance in such state. Further, the term "gelling agent composition" is used herein to mean a composition capable of gelling a medium when dissolved or dispersed in the medium. The term "gel composition" used herein means a gel comprising at least a gelling agent composition and a medium as constituent elements.

BACKGROUND ART

Dibenzylidene sorbitol derivatives or dibenzylidene xylitol derivatives even used in a small amount can gel a wide range of organic solvents or polymers (Kobayashi et al Journal of Japan Rheology Society, vol. 17, p.104 (1989) and Kobayashi et al, Journal of Japan Rheology Society, vol. 17, p.112 (1989)). These derivatives are used in a wide variety of applications, chiefly as solid marking agents, solid adhesives, effluent oil gelling agents, sol-gel transition type clarifying nucleating agents for polyolefins and so on. However, said derivatives are sparingly dissolved in water and can not be used as a gelling agent alone for water.

Various high molecular weight gelling agents useful in forming a heat-reversible water-containing gel are known and include non-electrolytic polymers such as natural high molecular weight starch or cellulose derivatives, electrolytic polymers such as alginic acid, agar and carrageenan, and protein-containing polymers such as gelatin, collagen and casein. Synthetic polymers such as copolymers of poval and sodium polyacrylate, semi-synthetic polymers such as starch-acrylic acid graft polymers, and the like are widely used as a water-absorbing polymer in the manufacture of paper diapers. However, natural materials have a drawback of decomposing. The gel-forming ability of electrolytic polymers is seriously affected by a salt and is markedly impaired in the presence of a salt. These polymers pose a problem of operational efficiency because they are dissolved in water usually at a low rate and a sol system is given an elevated viscosity.

Sericin, which is expensive and a specific species of amino acid, has an ability to gel water, but its gelling ability is markedly affected by the acidity of a system. Further, sericin involves a problem in terms of preservation. For these reasons, sericin has not been put to practical use.

When an aqueous medium is gelled using a conventional low molecular weight gelling agent, typically a dibenzylidene sorbitol derivative, an organic solvent is essentially used in combination.

In the above situation, there is an earnest desire for neutral low molecular weight organic gelling agents free from said defects, namely, those which can be stored without decomposition, do not adversely affect the environment, show high efficiency in a gel-forming process from a stage of sol formed on dissolution and are not affected by the presence of an inorganic salt.

DISCLOSURE OF THE INVENTION

An object of the present invention is to provide a novel useful low molecular weight organic gelling agent which is usable for gelling an aqueous medium.

Another object of the invention is to provide a gelling agent composition capable of easily gelling an aqueous medium even in the environment wherein a heat source can not be used.

In view of the foregoing situation, the inventors conducted extensive research on the aqueous medium-gelling properties of various low molecular weight organic compounds, and found that a sugar compound having a specific structure which is undisclosed in literature has a remarkable ability to specifically gel an aqueous medium. A further finding was that the organic gelling agent containing the sugar compound is a neutral low molecular weight organic gelling agent which not only has a gelling ability insusceptible to influence from the presence of an inorganic salt in a system but also can be stored without decomposition, and is unlikely to adversely affect the environment and capable of achieving a gel-forming process with high efficiency without elevation of viscosity in a sol stage. The present invention was completed based on these novel findings.

The sugar compound of the present invention is characterized by being represented by the formula (1) or the formula (2)

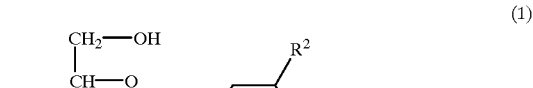

(1)

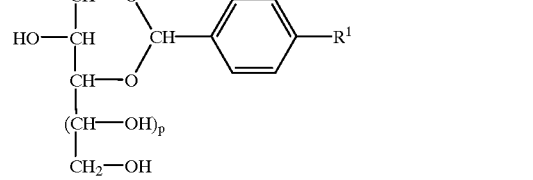

(2)

wherein R$^1$ and R$^2$ are the same or different and each represents an alkyl group having 1 to 3 carbon atoms, an alkoxyl group having 1 to 3 carbon atoms or a halogen atom, and p is 0 or 1.

The present inventors conducted extensive research on the aqueous medium-gelling properties of various low molecular weight organic compounds, and found that a composition of specific formula comprising a sugar compound of specific structure and a dispersant can form a gel when dissolved in an aqueous medium with heating and cooled, and also can easily form a gel approximately at room temperature without heating. Based on this novel finding, the present invention was accomplished.

The gelling agent composition of the invention comprises 100 parts by weight of at least one sugar compound selected from the group consisting of sugar compounds represented by the formula (1) and sugar compounds represented by the formula (2), and 1 to 1000 parts by weight of at least one dispersant selected from the group consisting of nonionic surfactants, anionic surfactants, cationic surfactants, amphoteric surfactants and hydrophilic organic solvents

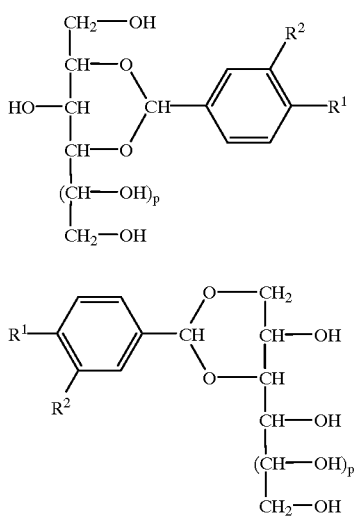

wherein $R^1$ and $R^2$ are the same or different and each represents an alkyl group having 1 to 3 carbon atoms, an alkoxyl group having 1 to 3 carbon atoms or a halogen atom, and p is 0 or 1.

Examples of the sugar compounds of the formula (1) or the formula (2) are mono(3-chloro-4-methylbenzylidene)-D-sorbitol, mono(3,4-dimethoxybenzylidene)-D-sorbitol, mono(3-ethyl-4-methylbenzylidene)-D-sorbitol, mono(3-methyl-4-ethylbenzylidene)-D-sorbitol, mono(3-propyl-4-methylbenzylidene)-D-sorbitol, mono(3,4-diethylbenzylidene)-D-sorbitol, mono(3,4-dichlorobenzylidene)-D-sorbitol, mono(3,4-dimethylbenzylidene)-D-sorbitol, mono(3,4-dipropylbenzylidene)-D-sorbitol, mono(3,4-diethoxybenzylidene)-D-sorbitol, mono(3,4-diisopropoxybenzylidene)-D-sorbitol and like sorbitol derivatives; and mono(3-ethyl-4-methylbenzylidene)-xylitol, mono(3-methyl-4-ethylbenzylidene)-xylitol, mono(3-propyl-4-methylbenzylidene)-xylitol, mono(3,4-diethylbenzylidene)-xylitol, mono(3,4-dichlorobenzylidene)-xylitol, mono(3,4-dimethylbenzylidene)-xylitol, mono(3,4-dipropylbenzylidene)-xylitol, mono(3-chloro-4-methylbenzylidene)-xylitol, mono(3,4-dimethoxybenzylidene)-D-xylitol and like xylitol derivatives.

The sugar compounds of the present invention can be prepared by the following process.

A process for preparing the contemplated sugar compound comprises the step of subjecting a sugar alcohol (A) and a benzaldehyde derivative (B) to dehydration condensation in water or in an organic solvent, said sugar alcohol (A) being at least one member selected from the group consisting of sorbitols and xylitols, and said benzaldehyde derivative (B) being at least one member selected from the group consisting of 3,4-disubstituted benzaldehyde represented by the formula (3) and dialkyl ether of 3,4-disubstituted benzaldehyde represented by the formula (4), the molar ratio (A/B) of the sugar alcohol (A) to the benzaldehyde derivative (B) being 2/1 to 1/2, thereby producing the contemplated sugar compound at a high reactivity and a high selectivity:

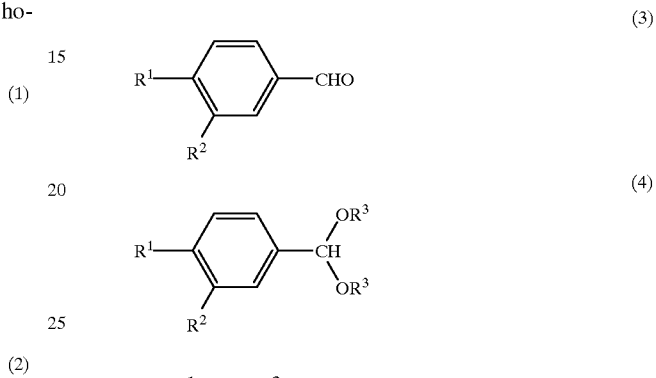

wherein $R^1$ and $R^2$ are the same or different and each represents an alkyl group having 1 to 3 carbon atoms, an alkoxyl group having 1 to 3 carbon atoms, or a halogen atom, and $R^3$ represents an alkyl group having 1 to 4 carbon atoms.

The sugar alcohol (A) is used preferably in the form of an aqueous solution in a concentration of 5 to 95% by weight, more preferably in the form of an aqueous solution in a concentration of 50 to 80% by weight.

Examples of the benzaldehyde derivative (B) are 3-chloro-4-methylbenzaldehyde, 3,4-dimethoxybenzaldehyde, 3-ethyl-4-methylbenzaldehyde, 3-methyl-4-ethylbenzaldehyde, 3-propyl-4-methylbenzaldehyde, 3,4-diethylbenzaldehyde, 3,4-dichlorobenzaldehyde, 3,4-dimethylbenzaldehyde, 3,4-dipropylbenzaldehyde, 3,4-diethoxybenzaldehyde, 3,4-diisopropoxybenzaldehyde, dimethyl ethers thereof, diethyl ethers thereof, dipropyl ethers thereof and dibutyl ethers thereof. Among them, 3,4-dimethylbenzaldehyde and 3,4-dichlorobenzaldehyde are preferred.

The molar ratio (A/B) of the reaction substrate to be used is in the range of 2/1 to 1/2. The concentration of the reaction substrate is preferably 5 to 90% by weight, more preferably 15 to 80% by weight.

The dispersing medium to be used in the reaction can be water or organic solvents such as cyclohexane, methyl cyclohexane, xylene, toluene or the like. It is suitable to use water from the viewpoints of yield, economy and the like. A powder of sorbitol or xylitol can be used as a reaction substrate in a reaction system wherein water is used as a dispersing medium.

Preferably the reaction is carried out in the presence of an acid catalyst. The acid catalyst to be used can be any of strongly acidic catalysts. Preferred strongly acidic catalysts are sulfuric acid, hydrochloric acid, ortho-, meta- or para-toluenesulfonic acid, alkyl (2 to 18 carbon atoms) benzenesulfonic acid, phosphoric acid and cationic exchange resin.

The amount of the catalyst to be used is not specifically limited, but is preferably in the range of 0.05 to 20% by weight, more preferably 1 to 10% by weight, based on the total amount of the reaction substrate (components (A)+(B)).

The reaction temperature is preferably 80° C. or lower, more preferably 15 to 40° C.

It is desirable to replace the air in the reaction system by a gas such as nitrogen or carbon dioxide gas which is inert to the benzaldehyde derivative to be used as the starting material.

The reaction time is not specifically limited, but usually 1 to 50 hours, preferably 3 to 10 hours.

After completion of the reaction, the reaction mixture is neutralized with an alkali while being stirred. The neutralized mixture is filtered, washed and dried. Useful alkalis are, for example, sodium hydroxide, potassium hydroxide, sodium carbonate, potassium carbonate, sodium hydrogencarbonate and sodium silicate. The alkalis can be used in the form of any of powders, granules and solutions. When the alkali is used in the form of a solution, the concentration thereof is not specifically limited, but is preferably 5 to 10% by weight. The solvent to be used for washing can be any of water, a solvent mixture of water and lower alcohol of 1 to 3 carbon atoms, hexane, cyclohexane, toluene, xylene and like organic solvents. Optionally, recrystallization can be further conducted.

The sugar compound of the formula (1) or the formula (2) prepared as above is very useful as a gelling agent for gelling an aqueous medium. The organic gelling agent of the present invention has a feature of containing at least one of said sugar compounds.

The sugar compounds of the present invention includes 1,3-O-isomer (corresponding to the compound of the formula (2)) and 2,4-O-isomer (corresponding to the compound of the formula (1)) as position isomers of 6-membered dioxane-type acetal ring. Any of these position isomers and mixtures thereof is effectively used as a gelling agent for gelling an aqueous medium. Among them, 2,4-O-(3,4-disubstituted benzylidene)-D-sorbitol and 2,4-O-(3,4-disubstituted benzylidene)-xylitol as 2,4-O-isomers are preferred from the viewpoints of the ability to gel an aqueous medium, and 2,4-O-(3,4-dimethylbenzylidene)-D-sorbitol and 2,4-O-(3,4-dimethylbenzylidene)-xylitol are more preferred.

The gel of the invention can be prepared by adding the organic gelling agent of the invention to the specified aqueous medium, heating the mixture to dissolve the gelling agent in the medium and cooling the solution.

The amount of the gelling agent to be used is not specifically limited. Although suitably selected according to the use of the gel, the amount is 0.02 to 10% by weight, preferably 0.4 to 5% by weight, based on the aqueous medium. Generally as the amount of the gelling agent increases, the hardness of the gel rises. When 1.8% by weight or less of the gelling agent is present, a clear gel is easily formed.

The heating temperature is not specifically limited but it is, at normal pressure, 100° C. or lower, preferably 50 to 100° C. At an elevated pressure (specifically, up to 50 kg/cm²G), it is 200° C. or lower, preferably 100 to 150° C.

In forming a gel, any desired cooling procedure, either slow cooling or rapid cooling, can be effected. Stated more specifically, when a sol (flowable solution) is cooled, a sol-gel transition occurs to give a non-flowable gel. The cooling temperature is 10 to 50° C., preferably 20 to 40° C.

The aqueous media to be gelled with the organic gelling agent of the invention include, for example, water, aqueous solutions, aqueous emulsions and aqueous dispersions. These media include aqueous solutions, aqueous emulsions and aqueous dispersions all of which contain a water-soluble polymer and/or inorganic salt. Also included are aqueous emulsions containing an ethylene-vinyl acetate copolymer. The aqueous media further include, for example, medium mixtures of water and a water-soluble medium (such as lower alcohol, dioxane, THF and the like). The concentration of the water-soluble polymer, inorganic salt or ethylene-vinyl acetate copolymer in the aqueous media is preferably 0.05 to 20% by weight.

When a water-soluble polymer exists as dissolved in an aqueous medium, the obtained gel has a higher gel hardness. Water-soluble polymers which can effectively increase the gel hardness include, for example, hydroxypropyl cellulose (number average molecular weight 10,000 to 500,000), hydroxyethyl cellulose (number average molecular weight 10,000 to 500,000), polyvinyl alcohol (number average molecular weight 400 to 100,000), polymethyl vinyl ether (number average molecular weight 400 to 100,000) and polyvinyl pyrrolidone (number average molecular weight 400 to 100,000).

The gel hardness can be increased when combinedly using conventional high molecular weight gelling agents such as starch, cellulose derivatives, alginic acid or agar.

One of the features of the gelling agent according to the invention is that the stability of the obtained gel and the hardness thereof are insusceptible to adverse influence from inorganic salts, alkalis, urea and surfactants present in the aqueous medium. Stated more specifically, a gel can be easily formed with substantially no influence on the gel hardness, when any of the following media is used, as when water is used: an aqueous medium having dissolved or dispersed therein a salt containing nitrogen, phosphorus, potassium (such as calcium nitrate, sodium nitrate, calcium phosphate, ammonium phosphate and potassium phosphate), urea or a salt thereof or the like; a 1% by weight aqueous solution of sodium chloride such as sea water; or an aqueous solution of a surfactant such as alkyl sulfate, alkyl ether sulfate, polyoxyethylene alkyl ether, quaternary ammonium salt, amphoteric surfactants and the like. It is seen from the above that the gelling agent of the invention can be used as a material for a water-retaining sanitary napkin as effectively as a water-absorbing polymer and as a water-holding agent in the field of civil engineering.

An aqueous emulsion of an ethylene-vinyl acetate copolymer, an aqueous solution of polyvinyl alcohol or an aqueous solution of polyvinyl pyrrolidone can easily form a gel in the presence of the gelling agent of the invention. A gel can be prepared in the form of a stick and can be filled in a container as such. The gel is useful as a solid bonding agent or solid adhesive.

A gel which is used for a medical purpose such as a poultice can be produced by gelling an aqueous medium containing a percutaneous drug, e.g. an antiphlogistic analgesic. Useful antiphlogistic analgesics are, for example, methyl salicylate, glycol salicylate and others such as alkyl ester of salicylic acid, hydroxyalkyl ester of salicylic acid, menthol or camphor. The amount of these antiphlogistic analgesics in the aqueous medium is 0.5 to 30% by weight, preferably 3 to 15% by weight.

A gel which is useful for a cosmetic purpose can be prepared by gelling an aqueous medium containing a surfactant, a humectant, a ultraviolet absorber or like active components for cosmetic compositions. Cosmetic gels can be used as a hair styling agent, makeup remover, facial cleaning composition, facial pack auxiliary, nail polish, nail polish remover, lipstick, deodorant (including a stick-shaped product), etc.

The gelling agent of the invention can be widely used in other applications, e.g. as artificial snow, low-temperature preservatives (materials for keeping cool), culture media, solid flavoring agents, solid agricultural insecticides, solid fertilizers, water-retaining gels for transformation of dessert into green land, aromatics, deodorants, artificial gel feeds, coagulants, gel flame retardants, battery electrolyte gels, gel marking agents, inks, coating compositions and so on.

The novel sugar compounds of the invention are very useful as a gelling agent for aqueous media.

The gelling agent composition of the invention comprises 100 parts by weight of said sugar compound and 1 to 1000 parts by weight of the dispersant.

The dispersant accelerates dispersing the sugar compound as a gelling component in the medium, promotes the formation of a gel, enhances a gel-forming rate and increases the gel strength.

Dispersants to be used in the invention are, for example, nonionic surfactants, anionic surfactants, cationic surfactants, amphoteric surfactants and hydrophilic organic solvents. These dispersants can be used in the invention either alone or in combination.

Examples of nonionic surfactants to be used as the dispersant are polyoxyalkylene alkyl ether, polyoxyalkylene alkenyl ether, polyoxyalkylene aryl ether, polyoxyalkylene polyol ether, polyoxyalkylene fatty acid ester, fatty acid amide, polyol ester, alkyl polyglycoside, amine oxide, etc.

Among the nonionic surfactants to be used in the invention, polyoxyalkylene alkyl ether, polyoxyalkylene alkenyl ether and polyoxyalkylene aryl ether are compounds of the formula (5) prepared by an addition reaction wherein an alcohol is reacted with an alkylene oxide:

$$R^4-O-(AO)_n-H \tag{5}$$

wherein $R^4$ is a straight-chain or a branched-chain alkyl group having 6 to 20 carbon atoms, an alkenyl group having 6 to 20 carbon atoms or an aryl group, A is an alkylene group having 2 to 4 carbon atoms, and n is an average molar number of added oxyalkylene groups and is 0.1 to 40.

Specific examples of the polyoxyalkylene alkyl ether having a straight-chain alkyl group are polyoxyethylene hexyl ether, polyoxypropylene hexyl ether, polyoxybutylene hexyl ether, polyoxyethylene heptyl ether, polyoxypropylene heptyl ether, polyoxybutylene heptyl ether, polyoxyethylene octyl ether, polyoxypropylene octyl ether, polyoxybutylene octyl ether, polyoxyethylene nonyl ether, polyoxypropylene nonyl ether, polyoxybutylene nonyl ether, polyoxyethylene decyl ether, polyoxypropylene decyl ether, polyoxybutylene decyl ether, polyoxyethylene undecyl ether, polyoxypropylene undecyl ether, polyoxybutylene undecyl ether, polyoxyethylene dodecyl ether, polyoxypropylene dodecyl ether, polyoxybutylene dodecyl ether, polyoxyethylene tridecyl ether, polyoxypropylene tridecyl ether, polyoxybutylene tridecyl ether, polyoxyethylene tetradecyl ether, polyoxypropylene tetradecyl ether, polyoxybutylene tetradecyl ether, polyoxyethylene pentadecyl ether, polyoxypropylene pentadecyl ether, polyoxybutylene pentadecyl ether, polyoxyethylene hexadecyl ether, polyoxypropylene hexadecyl ether, polyoxybutylene hexadecyl ether, polyoxyethylene heptadecyl ether, polyoxypropylene heptadecyl ether, polyoxybutylene heptadecyl ether, polyoxyethylene octadecyl ether, polyoxypropylene octadecyl ether and polyoxybutylene octadecyl ether.

Specific examples of the polyoxyalkylene alkyl ether having a branched-chain alkyl group are polyoxyethylene-(2-ethylhexyl) ether, polyoxypropylene-(2-ethylhexyl) ether, polyoxybutylene-(2-ethylhexyl) ether, polyoxyethylene isooctyl ether, polyoxypropylene isooctyl ether, polyoxybutylene isooctyl ether, polyoxyethylene isoheptyl ether, polyoxypropylene isoheptyl ether, polyoxybutylene isoheptyl ether, polyoxyethylene isononyl ether, polyoxypropylene isononyl ether, polyoxybutylene isononyl ether, polyoxyethylene isodecyl ether, polyoxypropylene isodecyl ether, polyoxybutylene isodecyl ether, polyoxyethylene isoundecyl ether, polyoxypropylene isoundecyl ether, polyoxybutylene isoundecyl ether, polyoxyethylene isododecyl ether, polyoxypropylene isododecyl ether, polyoxybutylene isododecyl ether, polyoxyethylene isotridecyl ether, polyoxypropylene isotridecyl ether, polyoxybutylene isotridecyl ether, polyoxyethylene isotetradecyl ether, polyoxypropylene isotetradecyl ether, polyoxybutylene isotetradecyl ether, polyoxyethylene isopentadecyl ether, polyoxypropylene isopentadecyl ether, polyoxybutylene isopentadecyl ether, polyoxyethylene isohexadecyl ether, polyoxypropylene isohexadecyl ether, polyoxybutylene isohexadecyl ether, polyoxyethylene isoheptadecyl ether, polyoxypropylene isoheptadecyl ether, polyoxybutylene isoheptadecyl ether, polyoxyethylene isooctadecyl ether, polyoxypropylene isooctadecyl ether, polyoxybutylene isooctadecyl ether, polyoxyethylene-(2-hexyldecyl) ether, polyoxypropylene-(2-hexyldecyl) ether, polyoxybutylene-(2-hexyldecyl) ether, polyoxyethylene-(2-octyldodecyl) ether, polyoxypropylene-(2-octyldodecyl) ether and polyoxybutylene-(2-octyldodecyl) ether.

Specific examples of the polyoxyalkylene alkenyl ether are polyoxyethylene oleyl ether, polyoxypropylene oleyl ether and polyoxybutylene oleyl ether.

Specific examples of the polyoxyalkylene aryl ether are polyoxyethylene-p-octylphenyl ether, polyoxypropylene-p-octylphenyl ether, polyoxybutylene-p-octylphenyl octylphenyl ether, polyoxyethylene-p-nonylphenyl ether, polyoxypropylene-p-nonylphenyl ether, polyoxybutylene-p-nonylphenyl ether, polyoxyethylene-p-dodecylphenyl ether, polyoxypropylene-p-dodecylphenyl ether and polyoxybutylene-p-dodecylphenyl ether.

The molar number of the alkylene oxide reacted in the addition reaction is generally expressed in terms of an average value. An average molar number thereof is 0.1 to 40 moles, preferably 2 to 20 moles.

Among said polyoxyalkylene alkyl ethers and polyoxyalkylene alkenyl ethers, those which are about 5 to about 20 in HLB are preferred. Of such polyoxyalkylene alkyl ethers and polyoxyalkylene alkenyl ethers, preferred is an addition reaction product of saturated or unsaturated alcohol of 10 to 20 carbon atoms with an average of 2 to 20 moles of alkylene oxide.

Examples of the polyoxyalkylene polyol ether to be used as the dispersant are compounds prepared by an addition reaction wherein an alkylene oxides such as ethylene oxide, propylene oxide or butylene oxide is reacted with a saccharide such as glucose, fructose or sucrose, a sugar alcohol such as sorbitol, xylitol or maltitol, a diol such as ethylene glycol or propylene glycol, a polyol such as glycerin, pentaerythritol or trimethylolpropane. Among them, preferred is a compound prepared by an addition reaction wherein an average of about 1 to about 50 moles of alkylene oxide is reacted.

Examples of the polyoxyalkylene fatty acid ester to be used as the dispersant include a compound prepared by an addition reaction wherein saturated or unsaturated fatty acid of 8 to 20 carbon atoms is reacted with an average of 0.1 to 40 moles of alkylene oxide of 2 to 4 carbon atoms. Preferred is a compound prepared by an addition reaction wherein saturated or unsaturated fatty acid of 8 to 18 carbon atoms is reacted with an average of 2 to 20 moles of alkylene oxide, such as polyoxyethylene oleyl ester.

Fatty acid amides useful as the dispersant include, for example, alkanolamide (alkanol of 1 to 6 carbon atoms) of saturated or unsaturated fatty acid of 8 to 20 carbon atoms. Preferred is lower alkanolamide (alkanol of 2 to 4 carbon atoms) of saturated or unsaturated fatty acid of 12 to 18 carbon atoms.

Further usable as the dispersant is a derivative prepared by an addition reaction wherein said fatty acid amide is reacted with an average of 1 to 40 moles of alkylene oxide.

Examples of the polyol ester to be used as the dispersant are esters of fatty acids of 2 to 18 carbon atoms with a saccharide such as glucose, fructose or sucrose, a sugar alcohol such as sorbitol, xylitol or maltitol, a diol such as ethylene glycol or propylene glycol, or a polyol such as glycerin, pentaerythritol or trimethylolpropane. Preferred is a polyol ester of fatty acid of 12 to 18 carbon atoms.

Further usable as the dispersant is a fatty acid ester of polyol prepared by an addition reaction wherein said polyol is reacted with an average of 1 to 40 moles of alkylene oxide.

An alkyl polyglycoside useful as the dispersant is represented by the formula (6)

$$(G)_m\text{—}O\text{—}R \tag{6}$$

wherein G is a pentose or a hexose, m is an average polymerization degree of the sugar, and 1 to 10, and $R^5$ is an alkyl group or an alkenyl group each having 6 to 20 carbon atoms.

Examples of the alkyl polyglycoside are decyl polyglucoside, dodecyl polyglucoside, tetradecyl polyglucoside, decyl polygalactoside, dodecyl polygalactoside, tetradecyl polygalactoside, decyl polyfructoside, dodecyl polyfructoside and tetradecyl polyfructoside.

The average polymerization degree of the alkyl polyglycoside is 1 to 10 moles, preferably 1 to 3.0 moles. A preferred HLB of the alkyl polyglycosides is selected from the range of about 10 to about 15.

Further usable as the dispersant is a derivative prepared by an addition reaction wherein said alkyl polyglycoside is reacted with an average of 1 to 40 moles of alkylene oxide.

The amine oxide to be used as the dispersant is represented by the formula (7)

$$R^6\text{—}N(R^7)(R^8)\text{—}O \tag{7}$$

wherein $R^6$ is an alkyl group or an alkenyl group each having 6 to 18 carbon atoms and each of $R^7$ and $R^8$ is a methyl group or an ethyl group.

Among the amine oxides, an amine oxide having an alkyl group of 10 to 12 carbon atoms is preferred from the viewpoint of dispersibility.

Examples of the anionic surfactant to be used as the dispersant are alkyl or alkenyl sulfate, alkyl ether sulfate, alkyl phenyl ether sulfate, alkyl benzenesulfonic acid salt, sulfosuccinic acid ester salt, metal salt of fatty acid and alkyl or alkenyl ether carboxylic acid salt.

Among them, preferred from the viewpoint of dispersibility are alkyl or alkenyl sulfate having about 12 to about 20 carbon atoms, alkyl ether sulfate having about 12 to about 20 carbon atoms, and sodium salt of fatty acid having an alkyl group or an alkenyl group each having about 12 to about 20 carbon atoms.

Examples of the cationic surfactant to be used as the dispersant are quaternary ammonium salt, especially tetraalkyl ammonium salt, and ammonium salt prepared by an addition reaction of alkylene oxide.

Among them, preferred from the viewpoint of dispersibility are trimethyl alkyl ammonium chloride having an alkyl group of 12 to 18 carbon atoms, dimethyl dialkyl ammonium chloride having two alkyl groups of 12 to 18 carbon atoms, and N,N-bis(polyoxyethylene)alkyl methyl ammonium chloride having an alkyl group of 12 to 18 carbon atoms.

Amphoteric surfactants useful as the dispersant include, for example, amino acid-based or betaine-based surfactants. Among them, preferred is alkyl dimethyl aminoacetic acid betaine having about 8 to about 20 carbon atoms.

The hydrophilic organic solvent to be used as the dispersant is a solvent which is homogenous when mixed with water in a desired ratio. Specific examples are polyalkylene glycol and polyhydric alcohol.

The polyalkylene glycol useful as the dispersant includes, for example, polyethylene glycol, polypropylene glycol, etc. A preferred polyalkylene glycol is a compound prepared by an addition reaction wherein about 0.1 to about 150 moles, preferably about 1 to about 100 moles, of alkylene oxide is reacted.

Polyhydric alcohols useful as the dispersant are, for example, saccharides such as glucose, fructose and sucrose, sugar alcohols such as sorbitol, xylitol and maltitol, diols such as ethylene glycol and propylene glycol, glycerin, pentaerythritol and trimethylolpropane.

The dispersant to be used in the invention can be in various forms such as crystals, powders, paste and solutions, and can be in any form insofar as the dispersant can be easily mixed with or dispersed in a medium (especially an aqueous medium) in a gelling agent composition. Essentially the dispersant is easily dissolved in an aqueous medium. For this reason, the dispersant in the form of fine crystals, powders, paste or solutions are preferred. More preferred is a dispersant as a solution.

The amount of the dispersant to be used in the invention is determined in a specific weight ratio relative to at least one sugar compound selected from the group consisting of sugar compounds of the formula (1) and sugar compounds of the formula (2) so that the amount of the dispersant is 1 to 1000 parts by weight, preferably 10 to 500 parts by weight, per 100 parts by weight of the sugar compound. When the dispersant is excessively used, the gelling ability is lowered in a non-heated system. On the other hand, a lesser amount of the dispersant tends to lower the dispersibility of the sugar compound in which case it is difficult to form a homogeneous gel.

To disperse the fine solids in a liquid, the dispersant has been conventionally used in a concentration in the vicinity of a critical micelle concentration (C.M.C.) (e.g. about 500 ppm or less) ("Surfactant", edited by Kodan Sha Scientific, published in 1979, pp.69–82). However, the dispersant is used in the invention to disperse the sugar compound in a concentration higher by one order of magnitude than C.M.C., namely in a high concentration of about 5000 ppm to about 15% by weight in which the dispersant can exhibit the dispersibility well.

If an aqueous medium is gelled using a sugar compound as a gelling agent without use of a dispersant, heating is required in gelling process or a prolonged period of time, e.g. at least 48 hours is involved in gelling at room temperature. On the other hand, since the gelling agent composition of the invention contains a large amount of the dispersant, namely at least 5000 ppm, a far larger amount than the conventional amount, the gelling time can be controlled so that the medium is gelled immediately or about 20 minutes after mixing the gelling agent composition with the aqueous medium in case of short time, or 120 minutes to 24 hours thereafter in case of deferred time.

On the other hand, the obtained gel composition has a markedly high gel hardness when formed at room temperature, compared with a gel obtained without use of a dispersant. Moreover, the above feature produces a surprising effect of extending the concentration range of the gelling agent to be used in gelling process.

This advantage may be presumably derived from the following phenomenon. When the gelling agent forms a three-dimensional network in the medium, the dispersant lodges in the structure of the network in a complicatedly entangled manner. Yet the detailed reason remains to be clarified.

Of the dispersants usable in the invention, a hydrophilic organic solvent is mixed with the sugar compound to make a composition. In this case, the hydrophilicity of the composition is enhanced, thereby causing the composition to become dispersed better in the aqueous medium.

The sugar compound dispersed by the dispersant and made easily wettable is combined in a complicated form with near-by water molecules due to the hydrogen bond to thereby enlarge the three-dimensional network throughout the system, so that the entire aqueous medium is gelled.

The gelling agent composition of the invention can be prepared by merely mixing the sugar compound and the dispersant.

The gelling agent composition of the invention can also be prepared by suspending the sugar compound and the dispersant in a small amount of a medium (in an amount substantially equal to the total amount of the sugar compound and the dispersant), aging the suspension at a temperature of 30 to 80° C., preferably 40 to 70° C. for 10 to 300 hours, preferably 24 to 200 hours, and optionally drying the obtained product.

The gelling agent composition of the invention can also be prepared merely by dissolving the sugar compound and the dispersant in a medium such as water with heating to give a sol, cooling the sol to a temperature ranging from room temperature to about 40° C. to produce a gel, and removing the medium from the gel at a temperature ranging from room temperature to 90° C. under a reduced pressure or normal pressure. The medium may be removed from the gel by freezing the gel and eliminating (lyophilizing) the medium from the frozen product under a pressure reduced below the vapor pressure of the frozen medium, e.g., at a pressure reduction degree of $10^{-2}$ mmHg.

The medium in which the sugar compound and the dispersant are suspended or dissolved includes, for example, aqueous media such as water, an aqueous solution of a salt and the like, lower alcohols having 1 to 4 carbon atoms such as methanol, ethanol, propanol and the like, dioxane and so on. Aqueous media are preferred among them.

A preferred process for preparing the gelling agent composition is, for example, a process comprising the steps of dissolving 100 parts by weight of at least one sugar compound selected from the group consisting of the sugar compound of the formula (1) and the sugar compound of the formula (2) and 10 to 500 parts by weight (preferably 20 to 400 parts by weight) of the dispersant in 5000 to 20000 parts by weight of water with heating, cooling the solution to 25° C. to form a gel, freezing the gel at a temperature of about −78° C. and removing the water under a reduced pressure (lyophilizing).

The form of the sugar compound to be used as the starting material in preparing the gelling agent composition of the invention is not specifically limited and includes, for example, granules, powders, fine particles, xerogel powders and so on. When the sugar compound and the dispersant are merely mixed together to give a gelling agent composition, xerogel powders are preferably adopted as the form of the sugar compound. The term "xerogel powder" used herein refers to a powder obtained by drying or lyophilizing the gel to remove the medium from the gel consisting of the sugar compound and the medium.

The gel composition can be prepared without heating the gelling agent composition of the invention.

That is, the gel composition can be easily prepared by adding an aqueous medium to the gelling agent composition of the invention.

In this case, while usually the gel composition can be easily prepared approximately at room temperature, it can be prepared by means of heating, ultrasonic wave irradiation or physical agitation by a homomixer or the like.

The aqueous media to be used in preparing the gel composition include water, aqueous solutions, aqueous emulsions and aqueous dispersions. A mixture of water and at least one medium other than water can be used. Examples of such media other than water are methanol, ethanol, propanol and like lower alcohols of about 1 to about 4 carbon atoms, dioxane, THF, cellosolve, etc.

The amount of the aqueous medium to be incorporated in the gel composition is 5 to 200 parts by weight, preferably 5 to 150 parts by weight, per part by weight of the gelling agent composition. If less than 5 parts by weight of the aqueous medium is used, there is a tendency to give a gel with the gelling agent precipitated. If over 200 parts by weight of the aqueous medium is used, the obtained gel is likely to become unstable because of its low strength.

The gelling agent composition or the gel composition of the invention may contain at least one additive selected from antioxidants, stabilizers and the like which do not impair the ability to form a gel.

Examples of the antioxidant are phenolic compounds, phosphite, sulfur compounds, etc. The amount of the antioxidant to be used is, for example, 0.001 to 3% by weight based on the gelling agent composition.

The stabilizer to be used is classified into two types, a stabilizer for the sugar compound and a stabilizer for the gel structure.

Examples of useful stabilizers for the sugar compound are alkaline compounds including inorganic alkali salts such as sodium hydroxide, potassium hydroxide, sodium carbonate, potassium carbonate or sodium salt of ethylenediaminetetraacetic acid (EDTA), salts of alkali metals such as potassium or sodium of organic acids such as citric acid, succinic acid, lactic acid, benzoic acid or fatty acid, and salts of alkaline earth metals such as magnesium or calcium of said organic acids. The amount of the stabilizer to be used is, for example, 0.001 to 3% by weight, based on the gelling agent composition.

The stabilizer for the gel structure to be used includes, for example, a chelating agent such as EDTA. The amount of the stabilizer to be used is, for example, 0.001 to 3% by weight based on the gelling agent composition.

The gelling agent composition or the gel composition of the invention may further contain at least one additive other than said additives such as inorganic salts, organic salts, flavoring agents, anticeptics, pigments, lower alcohols, surfactants other than the dispersants of the invention, polymers and so on.

The gelling agent composition or the gel composition of the invention may be used in combination with conventional other gelling agents including low molecular weight gelling agents such as dibenzylidene sorbitol, hydroxy-fatty acid derivatives, alkylamide derivatives or cholesterol derivatives, or high molecular weight gelling agents such as agar, gelatin or carageenan.

One of the features of the gelling agent composition in the present invention is that a gel can be easily formed in the invention without heating.

When a gel is formed using a gelling agent (i.e. sugar compound) and water as a solvent, the sugar compound is used in a concentration of up to about 2% by weight in view of the solubility of the sugar compound. If the concentration of the sugar compound is in excess of 1.8% by weight, a system containing the gel and crystals as mixed is produced. However, when a gel is formed using the gelling agent composition of the present invention, a gelling agent can be used in a high concentration and the obtained gel is stable in shape and higher in gel hardness.

Because the gelling agent composition of the invention can be easily gelled at room temperature, it can be used in applications as replacement products made of water-absorbing resins such as throw-away diapers and sanitary napkins, as products in the fields of water gel mats and cooling pillows, as coagulants for water treatment, as water-holding agents in civil engineering field, and as supports of cut flowers.

The gelling agent composition of the invention can easily gel an aqueous medium at room temperature, can easily form a gel in the environment lacking a heat source and can be used for various purposes.

BEST MODE FOR CARRYING OUT THE INVENTION

The present invention will be described below in more detail with reference to the following Examples.

The properties were determined according to the following methods.

Measurement of gel hardness

Measured with an instrument for measuring the agar jelly strength (manufactured by Kiya Seisakusho, Ltd.)

Measurement of melting point

Measured at a temperature-elevating rate of 1° C./min using an instrument for measuring the melting point of a minute amount of sample (manufactured by Yanagimoto Seisaku Sho Co., Ltd.)

Measurement of purity by gas chromatography (GC)

After pretreatment by reaction for conversion to trimethylsilyl derivative, the purity was measured by gas chromatography using columns of silicone fillers.

EXAMPLE 1

A 500 ml four-necked flask was charged with a 70 wt % aqueous solution of 143 g (0.55 mole) of D-sorbitol, 73.7 g (0.55 mole) of 3,4-dimethylbenzaldehyde and 12 g of 50 wt % sulfuric acid. The air inside the system was replaced with nitrogen gas. The contents of the flask were stirred at a temperature of 21° C. for 6 hours. The obtained reaction mixture was analyzed by GC. It was found that mono(3,4-dimethylbenzylidene)-D-sorbitol was produced in a yield of 70% and 0.5% or less of bis(3,4-dimethylbenzylidene)-D-sorbitol was also produced.

After standing for 24 hours, the reaction mixture was neutralized for 2 hours using 8.6 g of potassium hydroxide, and filtered to obtain cake. The cake was dispersed in 150 ml of toluene and was filtered again. After drying at 100° C. under a pressure ranging from normal pressure to 5 mmHg for 7 hours, 65 g of 2,4-O-(3,4-dimethylbenzylidene)-D-sorbitol was obtained with a purity of 99.5% as measured by GC (yield 39.7%). The product had a melting point of 199 to 200° C.

A 300 ml beaker was charged with 99 g of water and 1 g of the 2,4-O-(3,4-dimethylbenzylidene)-D-sorbitol obtained above. The mixture was heated to 96° C. with stirring. Two minutes later, a transparent homogenous solution (sol) was obtained. The solution (20 ml) was poured into a 300 ml sample beaker, and quenched in a water bath at 20° C., giving a transparent gel one minute later. In measurement three hours later, the gel hardness was 270 g/cm$^2$. The gel heated again to 96° C. heat-reversibly became a homogenous solution. When the solution was quenched in the same manner as above, the same gel was obtained again.

EXAMPLE 2

A 300 ml beaker was charged with 99 g of a 1 wt % aqueous solution of sodium chloride and 1 g of the 2,4-O-(3,4-dimethylbenzylidene)-D-sorbitol obtained in Example 1. The contents of the beaker were heated to 96° C. with stirring. Two minutes later, a transparent homogenous solution was obtained. The solution (20 ml) was poured into a 300 ml sample beaker, and quenched in a water bath at 20° C., giving a transparent gel one minute later. When measured three hours later, the gel hardness was 280 g/cm$^2$.

EXAMPLE 3

The same procedure as in Example 2 was repeated with the exception of using 99 g of a mixture of a 1 wt % aqueous solution of sodium nitrate, a 1 wt % aqueous solution of ammonium phosphate and a 1 wt % aqueous solution of potassium phosphate in equal amounts in place of the 1 wt % aqueous solution of sodium chloride, whereby a gel was formed. When measured three hours later, the gel hardness was 270 g/cm$^2$.

EXAMPLE 4

The same procedure as in Example 1 was repeated with the exception of using a 1 wt % aqueous solution of polyvinyl alcohol (number average molecular weight (Mn)= 700) in place of water, whereby a gel was formed. In measurement three hours later, the gel hardness was 470 g/cm$^2$.

EXAMPLE 5

The same procedure as in Example 1 was repeated with the exception of using a 25 wt % emulsion of a ethylene-vinyl acetate copolymer in place of water, whereby a gel was formed. In measurement three hours later, the gel hardness was 300 g/cm$^2$.

EXAMPLE 6

A 500 ml four-necked flask was charged with a 70 wt % aqueous solution of 120 g (0.55 mole) of D-xylitol, 73.7 g (0.55 mole) of 3,4-dimethylbenzaldehyde and 12 g of 50 wt % sulfuric acid. The air inside the system was replaced with nitrogen gas. The contents of the flask were stirred at a temperature of 21° C. for 6 hours. The obtained reaction mixture was analyzed by GC. It was found that mono(3,4-dimethylbenzylidene)-D-xylitol was produced in a yield of 70% and 0.5% or less of bis(3,4-dimethylbenzylidene)-D-xylitol was also produced. After standing 24 hours, the reaction mixture was neutralized for 2 hours using 8.6 g of potassium hydroxide, and filtered to obtain cake. The cake was dispersed in 150 ml of toluene and was filtered again. After drying at 100° C. under a pressure ranging from normal pressure to 5 mmHg for 7 hours, 44.5 g of 2,4-O-(3,4-dimethylbenzylidene)-D-xylitol was obtained with a purity of 99.2% as measured by GC (yield 30.1%). The product had a melting point of 179.5 to 180.0° C.

The same subsequent procedure as in Example 1 was repeated with the exception of using 2,4-O-(3,4-dimethylbenzylidene)-xylitol obtained above in place of 2,4-O-(3,4-dimethylbenzylidene)-D-sorbitol, giving a gel. When measured three hours later, the gel hardness was 250 g/cm$^2$.

EXAMPLE 7

The same procedure as in Example 2 was repeated with the exception of using 2,4-O-(3,4-dimethylbenzylidene)-xylitol in place of 2,4-O-(3,4-dimethylbenzylidene)-D-sorbitol, whereby a gel was formed. In measurement three hours later, the gel hardness was 240 g/cm$^2$.

EXAMPLE 8

A 500 ml four-necked flask was charged with a 70 wt % aqueous solution of 52 g (0.20 mole) of D-sorbitol, 35.0 g (0.20 mole) of 3,4-dichlorobenzaldehyde and 6 g of 50 wt % sulfuric acid. The air inside the system was replaced with nitrogen gas. The contents of the flask were stirred at a temperature of 21° C. for 6 hours. The obtained reaction mixture was analyzed by GC. It was found that mono(3,4-dichlorobenzylidene)-D-sorbitol was produced in a yield of 70% and 0.5% or less of bis(3,4-dichlorobenzylidene)-D-sorbitol was also produced. After standing for 24 hours, the reaction mixture was neutralized for 2 hours using 8.6 g of potassium hydroxide, and filtered to obtain cake. The cake was dispersed in 150 ml of toluene and was filtered again. After drying at 100° C. under a pressure ranging from normal pressure to 5 mmHg for 7 hours, 19.7 g of 2,4-O-(3,4-dichlorobenzylidene)-D-sorbitol was obtained with a purity of 99.2% as measured by GC (yield 29.2%). The product had a melting point of 202 to 205° C.

The same procedure as in Example 2 was repeated with the exception of using the above-obtained 2,4-O-(3,4-dichlorobenzylidene)-D-sorbitol in place of 2,4-O-(3,4-dimethylbenzylidene)-D-sorbitol, whereby a gel was formed. When measured three hours later, the gel hardness was 250 g/cm$^2$.

EXAMPLE 9

A 300 ml beaker was charged with 99.5 g of water and 0.5 g of the 2,4-O-(3,4-dimethylbenzylidene)-D-sorbitol obtained in Example 1. The contents of the beaker were heated to 90° C. with stirring. One minute later, a transparent homogenous solution was obtained. The solution (20 ml) was poured into a 300 ml sample beaker, and quenched in a water bath at 20° C., giving a transparent gel 8 hours later. Twenty four hours later, the gel hardness was 100 g/cm$^2$. The gel heated again to 90° C. heat-reversibly became a homogenous solution. When the solution was cooled, the same gel was formed 8 hours later.

EXAMPLE 10

A 300 ml four-necked flask was charged with 65 g of water, 20 g of glycerin, 5 g of glycol salicylate, 5 g of methyl salycylate and 5 g of L-menthol. The contents of the flask were stirred at room temperature to give a homogeneous solution. Added thereto was 1.5 g of a powder of the gelling agent obtained in Example 1 [2,4-O-(3,4-dimethylbenzylidene)-D-sorbitol]. The mixture was heated to 90° C. with stirring to obtain a solution. After cooling to 80° C., the solution was poured into a vat of stainless steel wherein it was further cooled to room temperature. Two minutes later, a gel of 2 mm thickness was formed. After the gel was cut to a sheet, 5×5 cm, the sheet was applied over the skin of bruised arm. Then the wounded part was covered with a wrapping sheet. Two minutes later, manifest antiphlogistic and analgesic effects were confirmed.

EXAMPLE 11

A 0.8 g quantity of the gelling agent powder obtained in Example 1 [2,4-O-(3,4-dimethylbenzylidene)-D-sorbitol] was added to 100 g of a 8 wt % aqueous solution of polyvinyl alcohol (Mn=10,000). The mixture was heated to 90° C. with stirring to obtain a sol. After cooling to 40° C., the sol was applied over human skin. Five minutes later, the sol coat was transformed into a gel coat. When the gel coat was peeled off, the soil over the skin was removed.

COMPARATIVE EXAMPLE 1

A sol was prepared in the same manner as in Example 11 with the exception of not using a gelling agent. The sol was applied over human skin, but the formation of a film took 30 minutes.

The properties in the following Examples and Reference Examples were determined by the methods described below.
Measurement of gel hardness The predetermined amount of a gel was prepared. The gel hardness of the gel 1 day or 1 month later was measured in a beaker, 4 cm in diameter and 6 cm in height using an instrument for measuring the agar jelly strength (manufactured by Kiya Seisakusho, Ltd.). Unless otherwise indicated, the concentration of the sugar compound of the gel compositions in the following Examples was 1% by weight. The gel hardness thus obtained was taken as a yield value. The higher the yield value was, the more stable the gel was. HLB value The HLB value of polyoxyalkylene alkyl ether was calculated by the equation of Griffin (W. C. Griffin, J. Soc. Cosmetic, Chemists, 1, 1180 (1949). The HLB values of nonionic surfactants other than polyoxyethylene alkyl ether were those shown in a brochure offered for sales.
Equation of Griffin $$HLB=20\times(\text{molecular weight of hydrophilic groups in surfactant}/\text{molecular weight of surfactant})$$

If the gel retains the original shape one month later, it was taken as stable.

EXAMPLE 12

Added to 100 ml of water were 1.0 g of 2,4-O-(3,4-dimethylbenzylidene)-D-sorbitol, 200 mg of CONION 275 (90) (trade name, product of New Japan Chemical Co., Ltd., an addition reaction product of an alcohol predominantly containing 12 carbon atoms with an average of 9 moles of ethylene oxide, HLB=13.5) and 10 mg of $K_2CO_3$. The three components were dissolved in water with heating at 98° C. (sugar compound/dispersant=1/0.2 (weight ratio)). The solution was cooled to 25° C., giving a gel composition. One day later, the gel composition had a gel hardness of 600 g/cm$^2$.

EXAMPLE 13

The gel composition obtained in Example 12 was frozen at −78° C. for 2 hours in a dry ice-acetone bath. Then the composition was dried under reduced pressure (pressure reduction degree of 10$^{-4}$ mmHg) (the procedure being hereinafter referred to as "lyophilized") with a vacuum pump for 24 hours to produce 1.2 g of a gelling agent composition as white powder.

EXAMPLE 14

When 10 ml of water was added to 140 mg of the gelling agent composition obtained in Example 13 (concentration of 1% by weight calculated as the sugar compound), the water was immediately gelled. One day later, the obtained gel composition had a gel hardness of 350 g/cm$^2$. One month later, the gel remained stable and showed a gel hardness of 380 g/cm$^2$.

EXAMPLE 15

When 10 ml of water was added to 400 mg of the gelling agent composition obtained in Example 13 (concentration of 3% by weight calculated as the sugar compound), the water was immediately gelled. One day later, the obtained gel composition had a gel hardness of 380 g/cm$^2$. One month later, the gel remained stable and showed a gel hardness of 400 g/cm$^2$.

EXAMPLE 16

Artificial urine (10 ml) was added to 140 mg of the gelling agent composition obtained in Example 13 (concentration of 1% by weight calculated as the sugar compound). The artificial urine was gelled in about 30 minutes. One day later, the obtained gel composition had a gel hardness of 260 g/cm$^2$. (Make-up of artificial urine: 1.94% by weight of urea, 0.8% by weight of sodium chloride, 0.06% by weight of calcium chloride, 0.11% by weight of magnesium sulfate and 97.09% by weight of water).

EXAMPLE 17

Added to 100 ml of water were 1.0 g of 2,4-O-(3,4-dimethylbenzylidene)-D-sorbitol, 1.0 g of CONION 275 (60) (trade name, product of New Japan Chemical Co., Ltd., an addition reaction product of an alcohol predominantly containing 12 carbon atoms with an average of 6 moles of ethylene oxide, HLB=11.5) and 10 mg of $K_2CO_3$. The three components were dissolved in water with heating at 98° C. (sugar compound/dispersant=1/1 (weight ratio)). The solution was cooled to 25° C., giving a gel composition. One day later, the gel composition had a gel hardness of 550 g/cm$^2$. The gel composition was frozen at −78° C. in a dry ice-acetone bath. Then the composition was lyophilized with a vacuum pump for 24 hours to produce 2.0 g of a gelling agent composition as white powder.

EXAMPLE 18

When 1.0 g of sand and 10 ml of water were added to 120 mg of the gelling agent composition obtained in Example 17, the water was immediately gelled. One day later, the obtained gel composition had a gel hardness of 350 g/cm$^2$. The same gel was formed in a pipe (made of acryl, 35 mm in inner diameter and 100 mm in length) which was erectly placed. Water was dropped into the gel from the top of the pipe but was unable to pass through the gel which showed a water-holding effect.

EXAMPLE 19

Added to 100 ml of water were 1.0 g of 2,4-O-(3,4-dimethylbenzylidene)-D-sorbitol, 2.0 g of CONION 275 (60) and 10 mg of $K_2CO_3$. The three components were dissolved in water with heating at 98° C. (sugar compound/dispersant=1/2 (weight ratio)). The solution was cooled to 25° C., giving a gel composition. One day later, the gel composition had a gel hardness of 600 g/cm$^2$. The gel composition was frozen at −78° C. in a dry ice-acetone bath. Then the composition was lyophilized with a vacuum pump for 24 hours to produce 2.98 g of a gelling agent composition as white powder.

EXAMPLE 20

When 10 ml of water was added to 300 mg of the gelling agent composition obtained in Example 19, the water was immediately gelled. One day later, the obtained gel composition had a gel hardness of 300 g/cm$^2$. One month later, the gel remained stable and showed a gel hardness of 350 g/cm$^2$.

EXAMPLE 21

Added to 100 ml of water were 1.0 g of 2,4-O-(3,4-dimethylbenzylidene)-D-sorbitol, 600 mg of sodium dodecylbenzene sulfonate (product of Nacalai Tesque Co., Ltd.) and 10 mg of $K_2CO_3$. The three components were dissolved in water with heating at 98° C. (sugar compound/dispersant=1/0.6 (weight ratio)). The solution was cooled to 25° C., giving a gel composition. One day later, the gel composition had a gel hardness of 450 g/cm$^2$. The gel composition was frozen at −78° C. in a dry ice-acetone bath. Then the composition was lyophilized with a vacuum pump for 24 hours to produce 1.6 g of a gelling agent composition as white powder.

EXAMPLE 22

When 10 ml of water was added to 120 mg of the gelling agent composition obtained in Example 21, the water was immediately gelled. One day later, the obtained gel composition had a gel hardness of 320 g/cm$^2$. One month later, the gel remained stable and showed a gel hardness of 320 g/cm$^2$.

EXAMPLE 23

Added to 100 ml of water were 1.0 g of 2,4-O-(3,4-dimethylbenzylidene)-D-sorbitol, 3.0 g of N-NON A 2020A5S (trade name, product of New Japan Chemical Co., Ltd., polyoxyethylene (20 moles reacted)-2-hexyldodecyl ether, HLB=15.2) and 10 mg of $K_2CO_3$. The three components were dissolved in water with heating at 98° C. (sugar compound/dispersant=1/3 (weight ratio)). The solution was cooled to 25° C., giving a gel composition. One day later, the gel composition had a gel hardness of 600 g/cm$^2$. The gel composition was frozen at −78° C. in a dry ice-acetone bath. Then the composition was lyophilized with a vacuum pump for 24 hours to produce 4.0 g of a gelling agent composition as white powder.

EXAMPLE 24

When 10 ml of water was added to 120 mg of the gelling agent composition obtained in Example 23, the water was immediately gelled. One day later, the obtained gel composition had a gel hardness of 280 g/cm$^2$. One month later, the gel remained stable and showed a gel hardness of 300 g/cm$^2$.

EXAMPLE 25

Added to 100 ml of water were 1.0 g of 2,4-O-( 3,4-dimethylbenzylidene)-D-sorbitol, 200 mg of Riponox 100 (trade name, product of Lion Co., Ltd., polyoxyethylene nonyl phenol, HLB (value shown in a brochure)=13.3) and 10 mg of $K_2CO_3$. The three components were dissolved in water with heating at 98° C. (sugar compound/dispersant= 1/0.2 (weight ratio)). The solution was cooled to 25° C., giving a gel composition. The gel composition was frozen at −78° C. in a dry ice-acetone bath. Then the composition was lyophilized with a vacuum pump for 24 hours to produce 1.2 g of a gelling agent composition as white powder.

EXAMPLE 26

When 10 ml of water was added to 120 mg of the gelling agent composition obtained in Example 25, the water was immediately gelled. One day later, the obtained gel composition had a gel hardness of 320 g/cm$^2$. One month later, the gel remained stable and showed a gel hardness of 330 g/cm$^2$.

EXAMPLE 27

Added to 100 ml of water were 1.0 g of 2,4-O-(3,4-dimethylbenzylidene)-D-sorbitol, 700 mg of APG-600 (trade name, product of Henkel Hakusui Co., Ltd., the alkyl chain length being that of alkyl polyglucoside predominantly containing 12 carbon atoms, average polymerization degree 1.4, HLB (value shown in a brochure)=13.5) and 10 mg of $K_2CO_3$. The three components were dissolved in water with heating at 98° C. (sugar compound/dispersant= 1/0.7 (weight ratio)). The solution was cooled to 25° C., giving a gel composition. The gel composition was frozen at −78° C. in a dry ice-acetone bath. Then the composition was lyophilized with a vacuum pump for 24 hours to produce 1.7 g of a gelling agent composition as white powder.

EXAMPLE 28

When 10 ml of water was added to 120 mg of the gelling agent composition obtained in Example 27, the water was immediately gelled. One day later, the obtained gel composition had a gel hardness of 320 g/cm$^2$. One month later, the gel remained stable and showed a gel hardness of 350 g/cm$^2$.

EXAMPLE 29

Added to 100 ml of water were 1.0 g of 2,4-O-(3,4-dimethylbenzylidene)-D-sorbitol, 200 mg of monolaurin (glycerin monolauric acid ester, product of Nacalai Tesque Co., Ltd.) and 10 mg of $K_2CO_3$. The three components were dissolved in water with heating at 98° C. (sugar compound/dispersant=1/0.2 (weight ratio)). The solution was cooled to 25° C., giving a gel composition. The gel composition was frozen at −78° C. in a dry ice-acetone bath. Then the composition was lyophilized with a vacuum pump for 24 hours to produce 1.2 g of a gelling agent composition as white powder.

EXAMPLE 30

When 10 ml of water was added to 120 mg of the gelling agent composition obtained in Example 29, the water was gelled in about 60 minutes. One day later, the obtained gel composition had a gel hardness of 220 g/cm$^2$. One month later, the gel remained stable and showed a gel hardness of 200 g/cm$^2$.

EXAMPLE 31

Added to 100 ml of water were 1.0 g of 2,4-O-(3,4-dimethylbenzylidene)-D-sorbitol, 200 mg of Amizol CDE (trade name, product of Kawaken Fine Chemical Co., Ltd., coconut oil fatty acid diethanolamide) and 10 mg of $K_2CO_3$. The three components were dissolved in water with heating at 98° C. (sugar compound/dispersant=1/0.2 (weight ratio)). The solution was cooled to 25° C., giving a gel composition. The gel composition was frozen at −78° C. in a dry ice-acetone bath. Then the composition was lyophilized with a vacuum pump for 24 hours to produce 1.2 g of a gelling agent composition as white powder.

EXAMPLE 32

When 10 ml of water was added to 120 mg of the gelling agent composition obtained in Example 31, the water was immediately gelled. One day later, the obtained gel composition had a gel hardness of 300 g/cm2. One month later, the gel remained stable and showed a gel hardness of 300 g/cm$^2$.

EXAMPLE 33

Added to 100 ml of water were 1.0 g of 2,4-O-(3,4-dimethylbenzylidene)-D-sorbitol and 500 mg of sodium oleate (product of Nacalai Tesque Co., Ltd.). The two components were dissolved in water with heating at 98° C. (sugar compound/dispersant=1/0.5 (weight ratio)). The solution was cooled to 25° C., giving a gel composition. The gel composition was frozen at −78° C. in a dry ice-acetone bath. Then the composition was lyophilized with a vacuum pump for 24 hours to produce 1.5 g of a gelling agent composition as white powder.

EXAMPLE 34

When 10 ml of water was added to 150 mg of the gelling agent composition obtained in Example 33, the water was gelled in about 60 minutes. One day later, the obtained gel composition had a gel hardness of 170 g/cm$^2$.

EXAMPLE 35

Added to 100 ml of water were 1.0 g of 2,4-O-(3,4-dimethylbenzylidene)-D-sorbitol and 200 mg of Arcard T-800 (trade name, product of Lion Co., Ltd., stearyl trimethyl ammonium chloride). The two components were dissolved in water with heating at 98° C. (sugar compound/ dispersant=1/0.2 (weight ratio)). The solution was cooled to 25° C., giving a gel composition. The gel composition was frozen at −78° C. in a dry ice-acetone bath. Then the composition was lyophilized with a vacuum pump for 24 hours to produce 1.2 g of a gelling agent composition as white powder.

EXAMPLE 36

When 10 ml of water was added to 200 mg of the gelling agent composition obtained in Example 35, the water was gelled in about 60 minutes. One day later, the obtained gel composition had a gel hardness of 100 g/cm$^2$.

EXAMPLE 37

Added to 100 ml of water were 1.0 g of 2,4-O-(3,4-dimethylbenzylidene)-D-sorbitol and 200 mg of RIKA-BION A 100 (trade name, product of New Japan Chemical Co., Ltd., lauryl dimethyl aminoacetic acid betaine). The two components were dissolved in water with heating at 98° C. (sugar compound/dispersant=1/0.2 (weight ratio)). The solution was cooled to 25° C., giving a gel composition. The gel composition was frozen at −78° C. in a dry ice-acetone bath. Then the composition was lyophilized with a vacuum pump for 24 hours to produce 1.2 g of a gelling agent composition as white powder.

EXAMPLE 38

When 10 ml of water was added to 150 mg of the gelling agent composition obtained in Example 37, the water was gelled in about 60 minutes. One day later, the obtained gel composition had a gel hardness of 100 g/cm$^2$.

EXAMPLE 39

Added to 100 ml of water were 1.0 g of 2,4-O-(3,4-dimethylbenzylidene)-D-sorbitol, 4.0 g of glycerin (product of Nacalai Tesque Co., Ltd.) and 10 mg of $K_2CO_3$. The three components were dissolved in water with heating at 98° C. (sugar compound/dispersant=1/4 (weight ratio)). The solution was cooled to 25° C., giving a gel composition. The obtained gel composition had a gel hardness of 240 g/cm$^2$. The gel composition was frozen at −78° C. in a dry ice-acetone bath. Then the composition was lyophilized with a vacuum pump for 24 hours to produce 5.0 g of a gelling agent composition as white powder.

EXAMPLE 40

When 10 ml of water was added to 500 mg of the gelling agent composition obtained in Example 39, the water was gelled in about 120 minutes. One day later, the obtained gel composition had a gel hardness of 80 g/cm$^2$.

EXAMPLE 41

Added to 100 ml of water were 1.0 g of 2,4-O-(3,4-dimethylbenzylidene)-D-sorbitol, 200 mg of polyethylene glycol #6000 (trade name, product of Nacalai Tesque Co., Ltd.) and 10 mg of $K_2CO_3$. The three components were dissolved in water with heating at 98° C. (sugar compound/dispersant=1/0.2 (weight ratio)). The solution was cooled to 25° C., giving a gel composition. The obtained gel composition had a gel hardness of 280 g/cm$^2$. Then the gel composition was dried under reduced pressure (2 mmHg) at 90° C. to produce 1.2 g of a gelling agent composition as white powder.

EXAMPLE 42

When 10 ml of water was added to 120 mg of the gelling agent composition obtained in Example 41, the water was gelled in about 360 minutes. One day later, the obtained gel composition had a gel hardness of 210 g/cm$^2$. One month later, the gel remained stable and showed a gel hardness of 200 g/cm$^2$.

EXAMPLE 43

After crushing 1.0 g of 2,4-O-(3,4-dimethylbenzylidene)-D-sorbitol into particles, the particles were mixed with 2.0 g of CONION 2P (50) (trade name, product of New Japan Chemical Co., Ltd., an addition reaction product of an alcohol predominantly containing 12 carbon atoms with an average of 5 moles of ethylene oxide, HLB=12.8) and 10 mg of $K_2CO_3$. After 4.0 ml of water was fully mixed with the mixture, the opening of the reactor was closed. The mixture was aged for 7 days at 50° C., whereby a gelling agent composition in the form of cake was obtained (sugar compound/dispersant=1/2 (weight ratio)).

EXAMPLE 44

When 10 ml of water was added to 1.0 g of the gelling agent composition obtained in Example 43, the water was gelled in about 60 minutes. One day later, the obtained gel composition had a gel hardness of 100 g/cm$^2$.

REFERENCE EXAMPLE 1

A 10 ml quantity of water was added to a mixture of 100 mg of 2,4-O-(3,4-dimethylbenzylidene)-D-sorbitol with 1 mg of $K_2CO_3$. The mixture was stirred at room temperature. After 24 hours, the mixture remained a suspension without forming a gel. The suspension, when heated to 98° C., was transformed into a sol. The sol was quenched to 25° C. to give a gel. One day later, the gel had a gel hardness of 280 g/cm$^2$.

REFERENCE EXAMPLE 2

The gel obtained in Reference Example 1 was cooled to −78° C. to freeze the gel. The water was removed by lyophilizing for 24 hours with a vacuum pump to produce a gelling agent in the form of powdery crystals (xerogel powder). The gelling agent thus obtained was suspended in 10 ml of water, whereby the particles were agglomerated. The agglomerate became a soft gel (sol-gel) in its periphery in about 48 hours so that the gel hardness was non-measurable (less than 60 g/cm$^2$).

EXAMPLE 45

Added to 1.0 g of the gelling agent in the form of xerogel powder obtained in Reference Example 2 were 1.0 g of Wandamine OX-300 (trade name, New Japan Chemical Co., Ltd., lauryl dimethylamine oxide) and 10 mg of $K_2CO_3$. A gelling agent composition (2.0 g) was obtained in the form of cake by mixing them (sugar compound/dispersant=1/1 (weight ratio)).

EXAMPLE 46

When 5.0 ml of water was added to 1.0 g of the gelling agent composition obtained in Example 45, the water was gelled in about 120 minutes. One day later, the obtained gel composition had a gel hardness of 80 g/cm$^2$.

REFERENCE EXAMPLE 3

Added to 10 ml of water were 300 mg of 2,4-O-(3,4-dimethylbenzylidene)-D-sorbitol and 10 mg of $K_2CO_3$ (concentration of the sugar compound: 3% by weight). The two components were dissolved in water with heating at 98° C. The solution was cooled to 25° C., whereby crystals were precipitated, resulting in failure to become a gel.

REFERENCE EXAMPLE 4

Added to 100 ml of water were 1.0 g of 2,4-O-(3,4-dimethylbenzylidene)-D-sorbitol, 4 mg of CONION 275 (90) and 10 mg of $K_2CO_3$. The three components were dissolved in water with heating at 98° C. (sugar compound/dispersant=1/0.004 (weight ratio)). The solution was cooled to 25° C., giving a gel composition. The gel composition was frozen at −78° C. in a dry ice-acetone bath for 2 hours. Then the composition was lyophilized with a vacuum pump for 24 hours to produce 1000 mg of a gelling agent composition as white powder. A 10 ml quantity of water was added to 100 mg of the gelling agent composition thus obtained, whereby the particles were agglomerated. The agglomerate became a soft gel (sol-gel) in its periphery in about 48 hours so that the gel hardness was non-measurable (less than 60 g/cm$^2$).

REFERENCE EXAMPLE 5

Added to 100 ml of water were 1.0 g of 2,4-O-(3,4-dimethylbenzylidene)-D-sorbitol, 11 g of CONION 275 (90) and 10 mg of $K_2CO_3$. The three components were dissolved in water with heating at 98° C. (sugar compound/dispersant=1/11 (weight ratio)). The solution was cooled to 25° C., but a gel was not formed.

What is claimed is:

1. A sugar compound represented by the formula (1) or the formula (2)

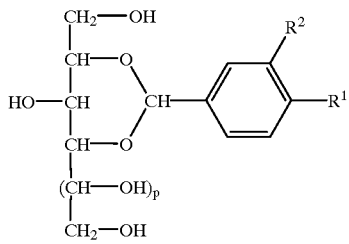
(1)

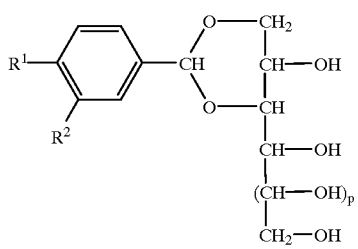
(2)

wherein $R^1$ and $R^2$ are the same or different and each represents an alkyl group having 1 to 3 carbon atoms, an alkoxyl group having 1 to 3 carbon atoms or a halogen atom, and p is 0 or 1.

2. The sugar compound according to claim 1, wherein each of $R^1$ and $R^2$ is a methyl group.

3. A process for preparing a sugar compound of the formula (1) or the formula (2), the process comprising the step of subjecting a sugar alcohol (A) and a benzaldehyde derivative (B) to dehydration condensation in water or in an organic solvent, said sugar alcohol (A) being at least one member selected from the group consisting of sorbitols and xylitols, and said benzaldehyde derivative (B) being at least one member selected from the group consisting of 3,4-disubstituted benzaldehyde represented by the formula (3) and dialkyl ether of 3,4-disubstituted benzaldehyde represented by the formula (4), the molar ratio (A/B) of the sugar alcohol (A) to the benzaldehyde derivative (B) being 2/1 to 1/2:

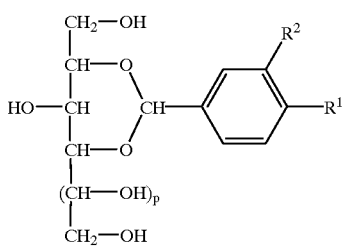
(1)

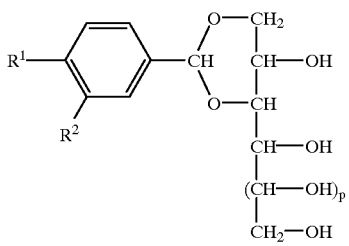
(2)

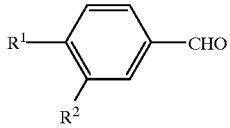
(3)

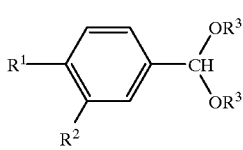
(4)

wherein $R^1$ and $R^2$ are the same or different and each represents an alkyl group having 1 to 3 carbon atoms, an alkoxyl group having 1 to 3 carbon atoms or a halogen atom, $R^3$ represents an alkyl group having 1 to 4 carbon atoms, and p is 0 or 1.

4. The process according to claim 3, wherein the dehydration condensation is carried out in the presence of an acid catalyst at a reaction temperature of not higher than 80° C.

5. An organic gelling agent comprising at least one sugar compound selected from the group consisting of sugar compounds represented by the formula (1) and sugar compounds represented by the formula (2):

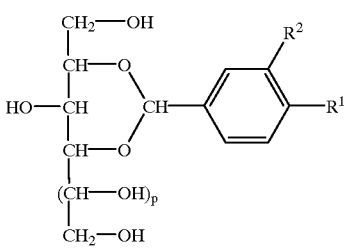
(1)

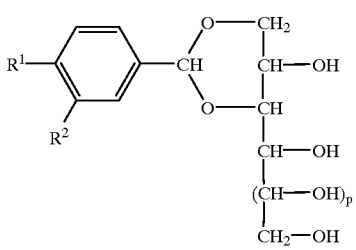
(2)

wherein $R^1$ and $R^2$ are the same or different and each represents an alkyl group having 1 to 3 carbon atoms, an alkoxyl group having 1 to 3 carbon atoms or a halogen atom, and p is 0 or 1.

6. A gel comprising an aqueous medium and an organic gelling agent comprising at least one sugar compound selected from the group consisting of sugar compounds represented by the formula (1) and sugar compounds represented by the formula (2):

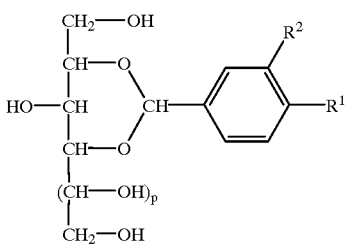
(1)

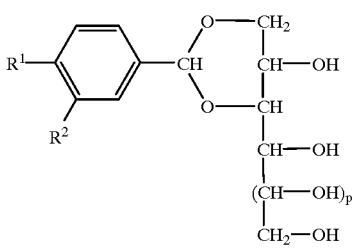
(2)

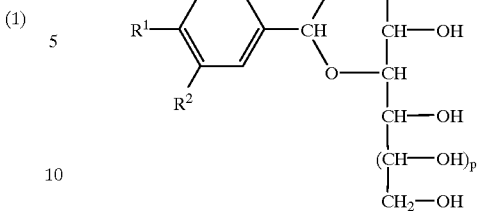
(2)

wherein $R^1$ and $R^2$ are the same or different and each represents an alkyl group having 1 to 3 carbon atoms, an alkoxyl group having 1 to 3 carbon atoms or a halogen atom, and p is 0 or 1.

7. The gel according to claim 6, wherein the aqueous medium is selected from the group consisting of: water, an aqueous solution, an aqueous emulsion and an aqueous dispersion.

8. The gel according to claim 6, wherein the aqueous medium comprises an aqueous solution, an aqueous emulsion or an aqueous dispersion any of which contains a water-soluble polymer and/or inorganic salt.

9. The gel according to claim 6, wherein the aqueous medium comprises an aqueous emulsion containing an ethylene-vinyl acetate copolymer.

10. A process for preparing a gel comprising dissolving an organic gelling agent comprising at least one sugar compound selected from the group consisting of sugar compounds represented by the formula (1) and sugar compounds represented by the formula (2) in an aqueous medium with heating to give a solution and cooling said solution:

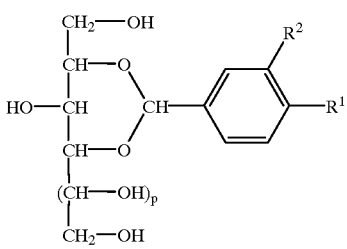
(1)

-continued wherein $R^1$ and $R^2$ are the same or different and each represents an alkyl group having 1 to 3 carbon atoms, an alkoxyl group having 1 to 3 carbon atoms or a halogen atom, and p is 0 or 1.

11. The gel according to claim 6 further comprising a percutaneous drug.

12. The gel according to claim 6 further comprising an active component for cosmetic compositions.

13. The gelling agent according to claim 5 comprising 100 parts by weight of said sugar compound and 1 to 1000 parts by weight of at least one dispersant selected from the group consisting of nonionic surfactants, anionic surfactants, cationic surfactants, amphoteric surfactants and hydrophilic organic solvents.

14. The gelling agent according to claim 13, wherein the gelling agent composition contains 10 to 500 parts by weight of the dispersant per 100 parts by weight of the sugar compound.

15. The gelling agent according to claim 13, wherein the sugar compound is in the form of a xerogel powder.

16. The gelling agent according to claim 13, wherein the dispersant is a nonionic surfactant.

17. The gelling agent according to claim 13, wherein each of $R^1$ and $R^2$ in the formula (1) or the formula (2) is a methyl group.

18. A process for preparing a gelling agent composition, the process comprising the steps of preparing a gel from at least one sugar compound selected from the group consisting of sugar compounds represented by the formula (1) and sugar compounds represented by the formula (2), a dispersant and a medium, and removing the medium from the gel:

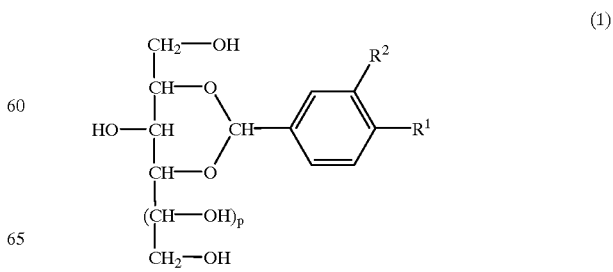
(1)

-continued

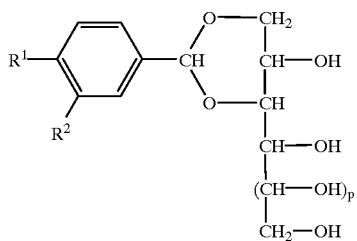
(2)

wherein $R^1$ and $R^2$ are the same or different and each represents an alkyl group having 1 to 3 carbon atoms, an alkoxyl group having 1 to 3 carbon atoms or a halogen atom, and p is 0 or 1.

19. The process according to claim 18, wherein the gel is frozen and the medium is removed from the frozen gel under a pressure reduced below the vapor pressure of the frozen medium.

20. The gel according to claim 6 wherein the gelling agent comprises 100 parts by weight of said sugar compound and 1 to 1000 parts by weight of at least one dispersant selected from the group consisting of nonionic surfactants, anionic surfactants, cationic surfactants, amphoteric surfactants and hydrophilic organic solvents.

21. The process according to claim 3, wherein the organic solvent comprises at least one member selected from the group consisting of cyclohexane, methyl cyclohexane, xylene and tolene.

22. The process according to claim 3, wherein the dehydration condensation is carried out in the presence of an acid catalyst in an amount of 0.05 to 20% by weight based on the total amount of the sugar alcohol (A) and the benzaldehyde derivative (B).

23. The process according to claim 3, wherein the dehydration condensation is carried out in the presence of an acid catalyst in an amount of 1 to 10% by weight based on the total amount of the sugar alcohol (A) and the benzaldehyde derivative (B).

\* \* \* \* \*